United States Patent [19]

Wagenknecht

[11] Patent Number: 5,160,335
[45] Date of Patent: Nov. 3, 1992

[54] PIN HOLDER SUPPORT

[75] Inventor: Marcel H. Wagenknecht, Le Lignon, Switzerland

[73] Assignee: Jaquet Orthopédie S.A., Geneva, Switzerland

[21] Appl. No.: 447,972

[22] Filed: Dec. 8, 1989

[30] Foreign Application Priority Data

Dec. 15, 1988 [CH] Switzerland .................. 04631/88

[51] Int. Cl.⁵ .................. A61B 17/56; A61B 17/58; A61B 17/60
[52] U.S. Cl. .................. 606/59; 606/57; 606/58
[58] Field of Search .................. 606/54–59, 606/72, 73

[56] References Cited

U.S. PATENT DOCUMENTS

| 2,393,694 | 1/1946 | Kirschner . |
| 4,488,542 | 12/1984 | Helland . |
| 4,600,000 | 7/1986 | Edwards .................. 606/59 X |
| 4,662,365 | 5/1987 | Gotzen et al. .................. 606/59 |
| 4,848,368 | 7/1989 | Kronner . |

FOREIGN PATENT DOCUMENTS

| 2520607 | 8/1983 | France . |
| 2557933 | 7/1985 | France . |
| 2559380 | 8/1985 | France .................. 606/54 |
| 2579688 | 10/1986 | France . |
| 2077847 | 12/1981 | United Kingdom . |
| 2110094 | 1/1983 | United Kingdom . |

Primary Examiner—Ronald Frinks
Attorney, Agent, or Firm—Peter C. Richardson; Lawrence C. Akers; Elizabeth O. Slade

[57] ABSTRACT

A pin holder support is provided which is suitable for external bone fixation utilizing pins inserted into bone. The device comprises a clamp for gripping the bone pins a deflection member, and a jaw which positions the device along a fixation bar. The deflection member is situated between the clamp and the jaw and has on one face, a rotation means for cooperation with a complementary means of the clamp or of the jaw such that the combination ensures rotatability of the clamp with respect to the jaw and, on its opposite face, a curved guide means for cooperation with a complementary curved means of the other of the jaw or of the clamp, respectively, so as to ensure ability of the clamp to swivel with respect to the jaw.

17 Claims, 4 Drawing Sheets

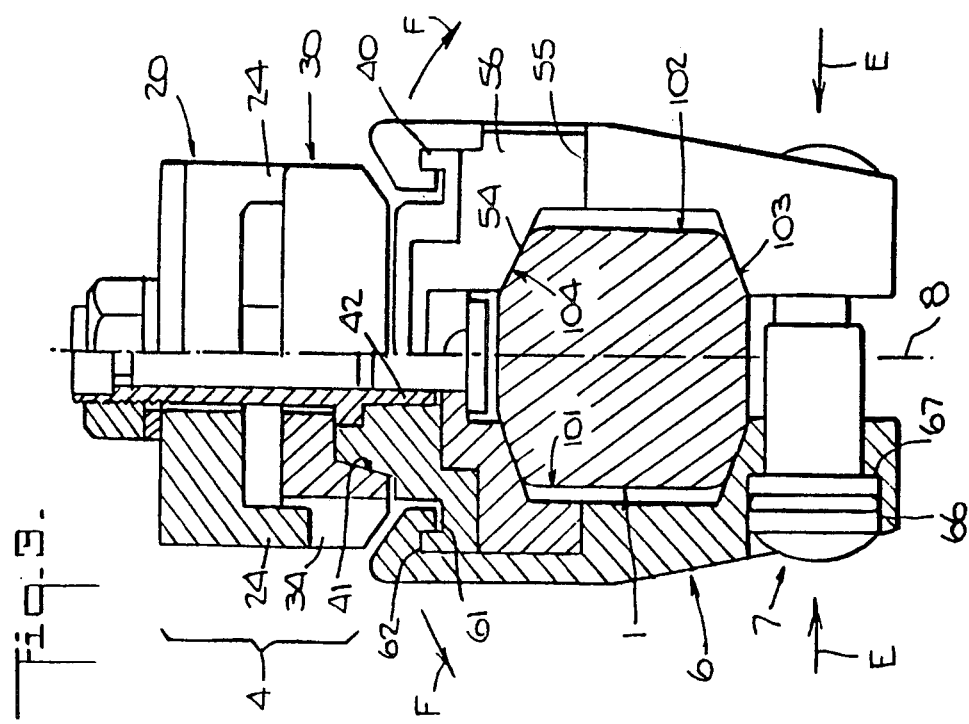
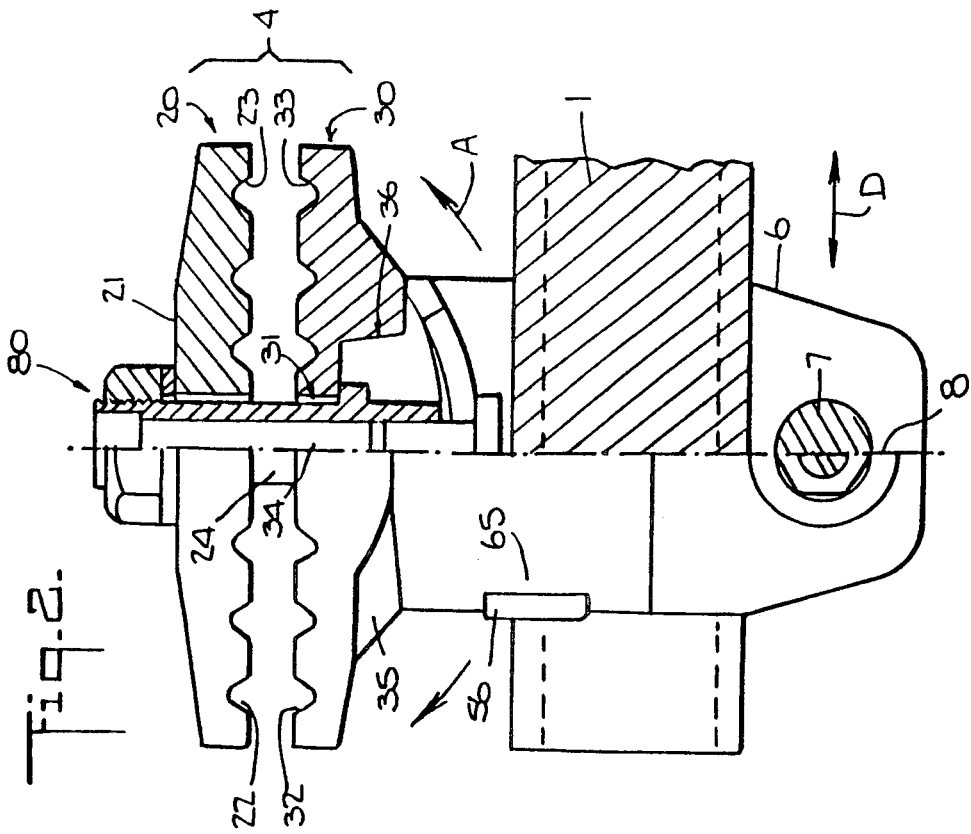

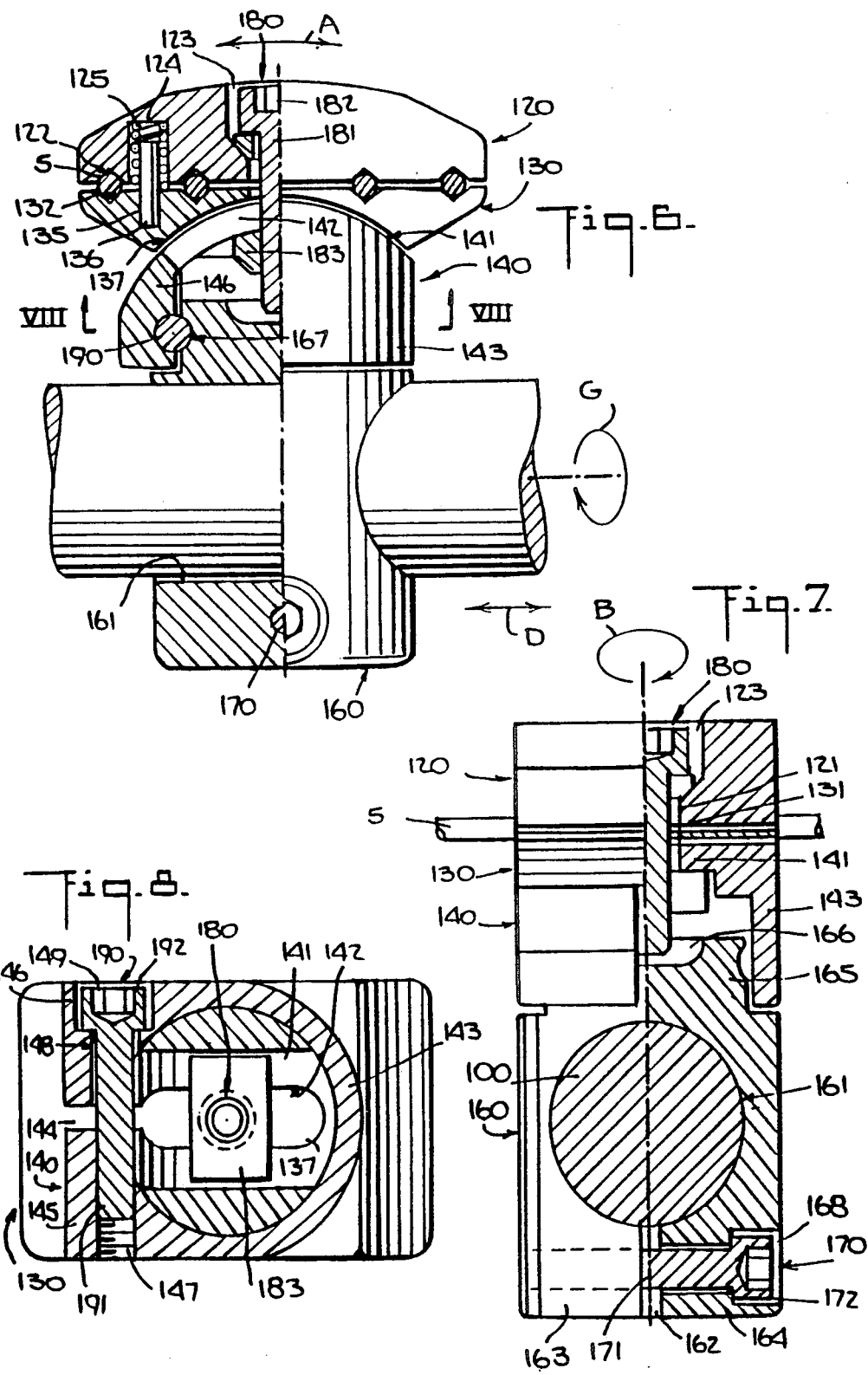

PIN HOLDER SUPPORT

BACKGROUND OF THE INVENTION

The present invention relates to the field of traumatology and orthopedics and more particularly has as its object a pin carrier clip intended for external bone fixation devices utilizing pins inserted into the bone. This is also referred to as a pin holder support.

By "traumatology" is understood casualty surgery and by "orthopedics" the correction of congenital malformations or malformations resulting from incorrectly aligned bone unions.

A number of devices permitting the transfer or displacement of a segment of a bone in relation to the remainder of the latter have been developed over a period of many years. Depending on circumstances the displacement required may be angular, longitudinal or rotational, or may comprise a combination of such displacements.

The devices used are mainly of two types: internal devices, which are introduced into the patient's body, and internal fixation means connected, by pins inserted into the bone, to the bone fragments requiring displacement or support.

These devices are always placed in position under anesthesia. In order to reduce the duration of the anesthesia to the minimum, it is endeavoured to develop devices which allow positioning at every possible angle, but which can easily be adjusted by a surgeon, who is not necessarily a mechanical expert.

The invention relates to the external fixation means connected to sets of pins inserted into each of the bone fragments which are to be positioned relative to each other, on each side of the fracture.

According to a first technique employed at the present time, hoop members are placed around the limb, the hoops being fastened on the one hand to pins or wires inserted into the bone and on the other hand to spacer bars between the hoops. Use is also made of frames disposed one on each side of the limb and connected by pins passing through the bone fragments.

According to another technique the pins are connected to a single fixation bar, which is disposed substantially parallel to the fractured bone. Each set of pins inserted into a bone fragment is clamped in a support, which is adapted to be oriented relative to the fixation bar and fixed to a fastening clip on said bar.

For the orientation of each set of pins, various systems of ball or universal joints are known, which have the disadvantage that their position cannot be continuously modified.

It has already been proposed to use parts having notched angular faces adapted to engage in corresponding parts, in relation to which they are fixed by connections means passing through a central bore, such as the system described in French Patent F-2,557,933. The articulation obtained with this system is however limited to the predetermined angular positions of the notches and in addition requires double adjustment, in two planes, in order to obtain the desired orientation, while furthermore the fastening of the pins is effected with an additional clamp system.

A pin carrier clip fastened to a curved guide member, as described in French Patent F-2,517,195, has also been proposed. The curved guide member is equipped with helical toothing intended for cooperation with a worm.

In addition, a device is also known which is composed of two members, one member being fastened to the pins and the other to the fixation bar, and one of them having a curved portion guiding the other, as described in American U.S. Pat. No. 4,628,922. This device requires the independent clamping of the pins and the locking in position of the members with the aid of independent clamp means.

SUMMARY OF THE INVENTION

The present invention proposes a clip for fastening a set of pins and for the angular positioning of the latter relative to a fixation or spacer bar, which clip comprises a clamp for gripping the pins, a deflection member, a jaw effecting positioning along the bar and blocking means in a wanted position.

It is characterized in that the deflection member is disposed between the clamp and the jaw and in that the deflection member has:
- on one face, rotation means intended to cooperate with complementary means of the clamp or of the jaw, to ensure the rotation of the clamp with respect to the jaw, and
- on the opposed face, curved guide means intended to cooperate with complementary curved means of the jaw or of the clamp respectively, to ensure the swivelling of the clamp with respect to the jaw.

In addition, it provides means for positioning the clip along the fixation bar, together with, in one embodiment, a clamping and unclamping limiter. In a variant the clip is slidable along the spacer bar.

The clamp enables the pins to be held in a plane while allowing their angular positioning relative to the fixation bar along which it is slidable, said fixation bar being disposed substantially parallel to the bone.

In order to reduce the minimum the discomfort caused to the patient by the external fixation means, it is endeavoured to reduce as much as possible the dimensions and the weight of its components.

In this description mention is made of a fractured bone, but it is obvious that the bone may also be one deliberately cut through, for example for the purpose of orthopedic elongation.

BRIEF DESCRIPTION OF THE DRAWINGS

The enclosed drawing shows by way of non-limitative example one embodiment of the present invention.

FIG. 2 shows a clip in a plane parallel to the axis of the bar, the pins being oriented perpendicularly. The components are shown in section on the right-hand half of FIG. 2, and in side view on the left-hand half.

FIG. 3 is a view of the clip in a plane at right angles to the axis of the bar, shown in section on the left-hand half of the figure and in side view on the right-hand half.

FIG. 6 is a variant for the clip according to the invention, in a plane parallel to the axis of the bar, shown in section on the left-hand half of the figure and in side view on the right-hand half.

FIG. 7 is a view of the clip in FIG. 6, in a plane transversal to the bar axis, shown in section on the right-hand half of the figure and in side view on the left-hand half.

FIG. 8 is a sectional view along VIII—VIII in FIG. 6.

DETAILED DESCRIPTION OF THE DRAWINGS

Figure 1:
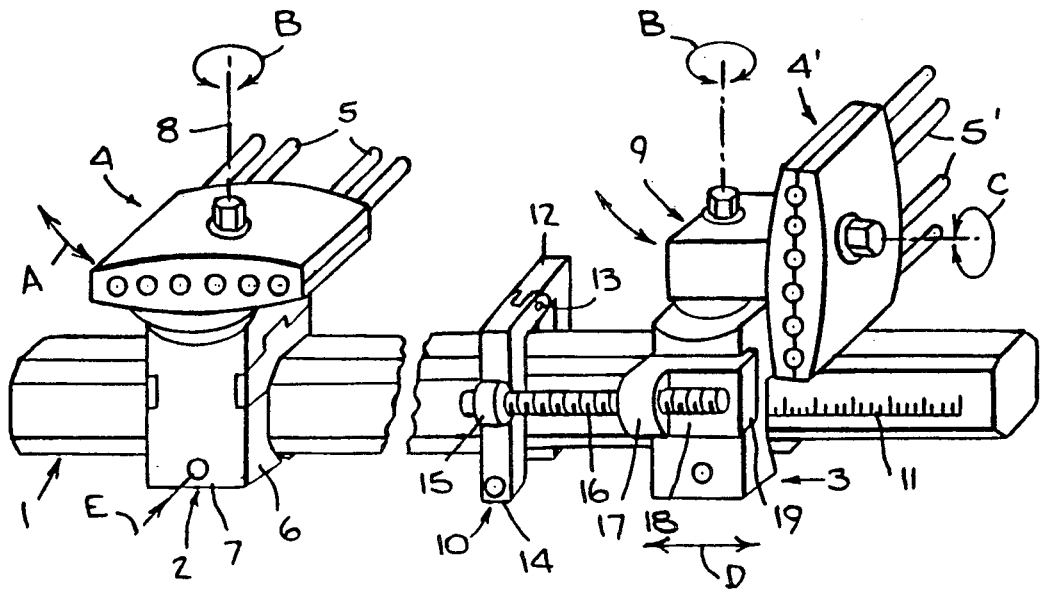
FIG. 1 is a general schematic view in perspective of pin carrier clips mounted on an external fixation bar, which is in addition provided with a device for the lateral displacement of one of the clips.

The general view shown in FIG. 1 illustrates an external fixation bar 1 of polygonal section, on which are disposed to clips 2 and 3 according to the invention, which are indirectly fastened to a clamp 4 gripping pins 5.

A continuous external fixation bar 1 is shown in the drawings, but it is obvious that as a variant the bar may be one consisting of telescopic elements.

Each clip is provided with a curved deflection member positioned between the clamp 4 and a jaw 6 surrounding the bar 1 on which it may be fixed by a positioning device 7. This curved deflection member is not shown in the schematic view given in FIG. 1, but will be described in detail later on. It permits the angular pivoting of the clamp 4 in the direction of the arrow A, on the one hand, and the continuous orientation by 0 to 360° of the set of pins relative to the clamping axis 8, in the direction of the arrow B, on the other hand.

The clip 3 shown in FIG. 1 is in addition provided with an angle drive means 9 enabling the clamp 4', and consequently the pins 51, to be turned 90°. An angle drive of this kind is for example used when the pins 51' are intended to be inserted into the epiphysis (for example the tibial or femoral head) of a bone whose diaphysis would receive the pins 5. In addition to the circular pivoting in the direction of the arrow A and the angular orientation in accordance with the arrow B, the clip 3 also permits angular orientation in accordance with the arrow C. The arrow D in turn represents the displacement of the clip along the bar.

In the schematic view shown in FIG. 1 a member 10 is also shown which serves for the displacement of the clip 3 along the bar 1, which may carry linear markings 11, usually graduated in millimeters.

The displacement member 10 consists of a fastening clip 12 comprising two parts pivoted on an axis 13 and is clamped on the bar 1 by a screw 14. It also comprises a support 15 fixed for rotation with the clip 12 and having an opening for the fastening of the head of a feed screw 16, along which is moved a threaded boss 17 integral with a clamp 18 provided with two flanges 19 intended to embrace the side portion of the clip 3.

Referring to FIGS. 2 and 3, the external fixation bar 1, the clamp 4, the jaw 6, the positioning device 7 enabling the clip to be fastened on the bar 1, and also an arrangement 80 for clamping the pins in the direction of the axis 8 can be seen again. The previously mentioned curved deflection member is shown under the general reference 40.

To go into detail the clamp 4 is composed of an upper grip 20 and a lower grip 30, both of which grips have a generally rectangular shape and are provided with a central passage 21, 31 for the clamping arrangement 80. The mutually facing surfaces of the grips are provided with parallel grooves 22, 32 intended to the passage of the pins inserted into the bone. It should be noted that the grooves 22 or 32 are provided in their central portion with a recess 23 or 33 intended to ensure better anchoring of the pins.

The upper clamp grip 20 is in addition provided with two downwardly projecting side nibs 24 intended to penetrate into corresponding recesses 34 in the lower grip, in such a manner as to prevent the rotation of the grips 20 and 30 in relation to one another.

The lower grip 30 of the clamp is provided in its bottom portion with a circular central boss 35, in which a central frustoconical recess 36, of which the angle is of the order of 7°, is formed.

Figure 4:
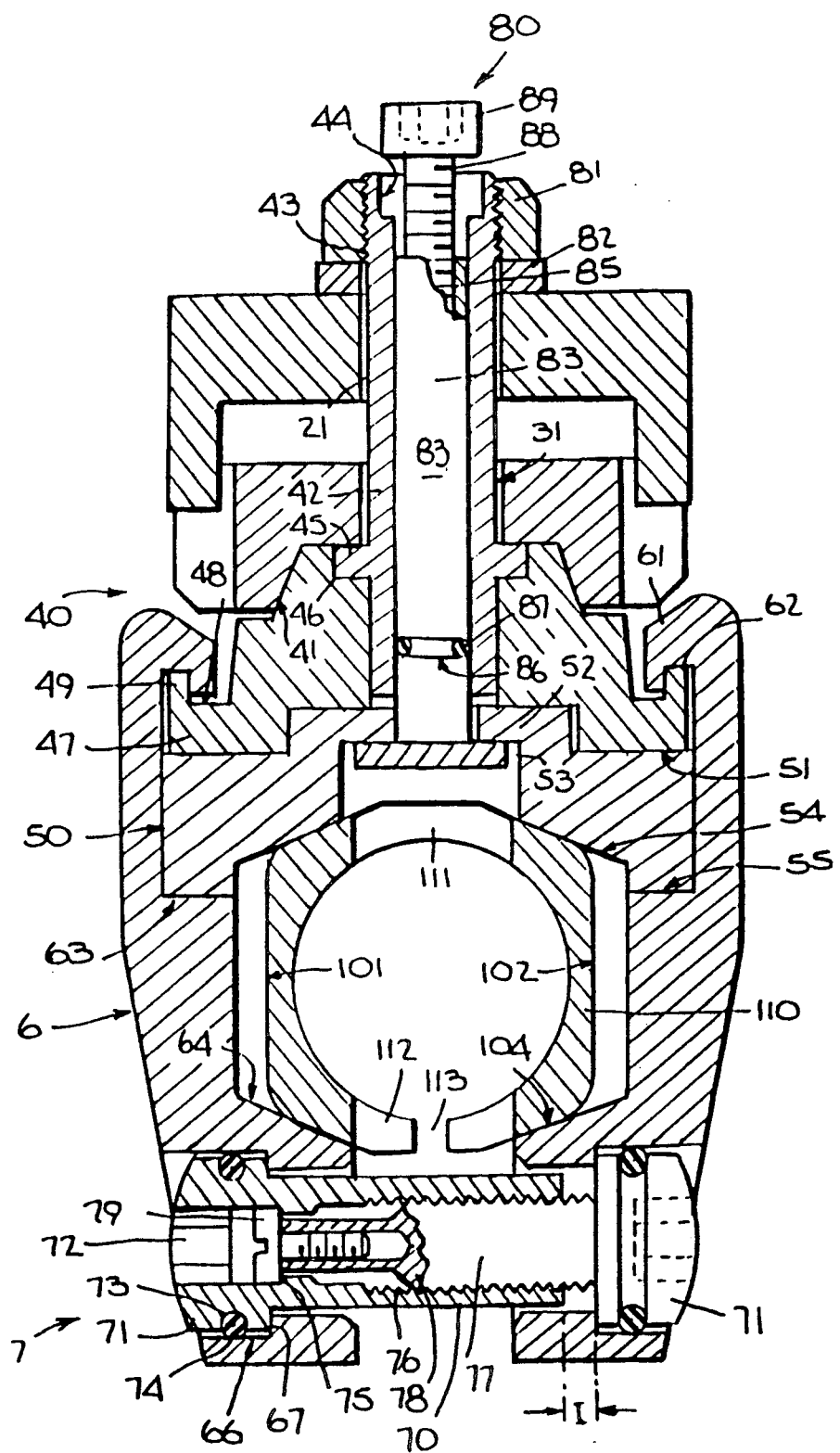
FIG. 4 is a view in section, on a larger scale, of the clip shown in FIG. 3.

The frustoconical recess 36 is intended to receive a corresponding frustoconical shoulder 41 on the curved deflection member 40, the central portion of which receives a hollow shaft 42 provided with an external screwthread 43 and an internal shoulder 44 in its end portion (see FIG. 4). The hollow shaft 42 is usually made of stainless steel and is sealed in the curved deflection member 40 by any means known to those versed in the art (for example screwing or adhesive bonding). In order to ensure correct positioning of the hollow shaft 42, a collar 45 may be provided for support in a corresponding cylindrical opening 46 provided in the top part of the deflection member 40. The hollow shaft 42 is intended to pass through the central passage 31 in the lower grip 30 and the central passage 21 in the upper grip 20 of the clamp 4.

The curved deflection member 40 has a radius of curvature whose centre is situated beyond the plane of the pins. In its bottom part it is provided with two curved skids 47, which are symmetrical and parallel and each of which has a groove 48 delimiting a curved shoulder 49 in the top part of each skid 47. As can be seen in the drawing, the curved skids 47, and consequently the curved shoulder 49, are disposed parallel to the axis of the bar.

The curved skids 47 are intended to slide along hollows 51 of corresponding curvature, which are formed in a bridge 50 disposed between the parts of jaw 6. The central portion 52 of the bridge is provided with an oblong opening 53 parallel to the skids 47.

In its bottom portion the bridge 50 is provided with two inclined sides 54 whose slope corresponds to the shape of the bar 1, and with two straight rim portions 55 having at each end an outwardly projecting flange 56 (FIGS. 2 and 3).

The clamshell type jaw 6 has two symmetrical parts, each of them has in its inner portion visible in FIG. 4:
- a curved shoulder 61 and a groove 62, which are intended to cooperate respectively with the groove 48 and the shoulder 49 of the deflection member 40;
- a straight rim 63 intended to bear against the corresponding rim portion 55 of the bridge 50;
- an inclined side 64 whose slope also corresponds to the shape of the bar 1.

As can be seen in FIG. 2, each jaw is provided above the straight rim portion with lateral recesses 65 intended to receive the lateral flanges 56 of the bridge 50. In its bottom portion each jaw is provided with an opening 66 having an inner rim 67 intended to cooperate with the positioning device 7.

This positioning device 7 will be described with reference to FIG. 4, which is more detailed. It comprises a hollow shaft 70 provided with a head 71 having an opening 72 leading to the outsided and intended to cooperate with a clamping tool, for example a hexagonal opening. The diameter of the head 71 is such that it penetrates into the opening 66 of the jaw and comes to bear against the inner rim 67. It will be observed that the head 71 is in addition provided with an external circular groove 73 intended to receive a ring 74 of the O-ring type.

The hollow shaft 70 is provided with an internal shoulder 75 and ends in a central internal screwthread 76.

The positioning device 7 also comprises a central shaft 77 having a head 71 identical to that previously described. The central shaft 77 is provided with an external screwthread intended to cooperate with the internal screwthread 76 of the hollow shaft 70, and is also provided with an internal screwthread 78 intended to receive a cheese-head screw (a British term, which is equivalent to the term "filister head screw" or "pan head screw") 79.

It will be observed in FIG. 4 that when the head of the screw 79 comes to bear against the internal shoulder 75, a gap i will be left between the end of the hollow shaft 70 and the inner face of the head 71 of the central shaft 77.

The clamping arrangement 80 consists of a nut 81 mounted on a washer 82 and intended to be screwed onto the screwthread 43 of the hollow shaft 42 which, as has already been seen, is fastened to the curved deflection member 40.

In the embodiment shown in FIG. 4 a central tube 83 has been disposed inside the hollow shaft 42. This central tube 83 ends at the bottom in a disc 84 and at the top in a central internal screwthread 85. The disc 84 is fixed to the end of the tube 83 by any means known to those versed in the art. It has a curved shape whose curvature corresponds to that of the central portion 52 of the bridge 50 against which it comes to bear, while the tube 83 passes freely through the oblong opening 53 in the bridge before penetrating into the hollow shaft 42.

The tube 83 is in addition provided with a groove 86 for the insertion of a ring 87 of O-ring type. The clamping arrangement 80 is completed by a screw 88, whose head 89 has a hexagonal opening and is of such dimensions as to bear against the internal shoulder 44 of the hollow shaft 42.

Figure 5:
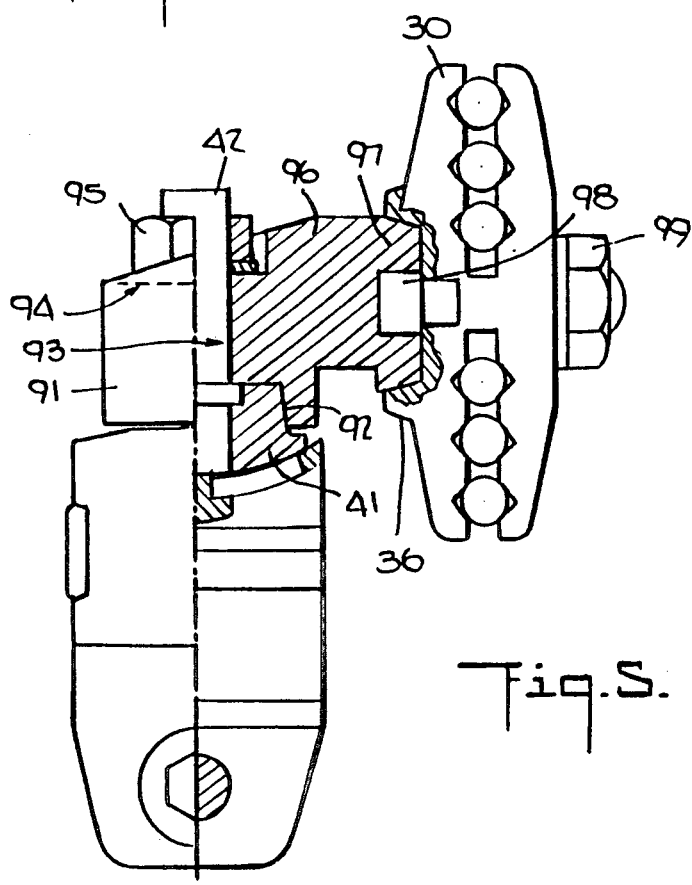
FIG. 5 is a partly sectional view, in a plane parallel to the axis of the bar, of a variant clip, showing an angle drive means enabling the pins to be oriented in other directions.

The angle drive 9 already schematically indicated in FIG. 1 is shown in detail in FIG. 5. It is an elongate member having at its base a collar 91 defining a frustoconical opening 92 whose shape corresponds to the conical shoulder 41 of the curved deflection member 40. At the centre of the collar a through opening 93 permits the passage of the hollow shaft 42 and leads onto a flat 94 intended to cooperate with a clamp nut 95. A protuberance 96 extends at right angles to the opening 93 and ends in a frustoconical shoulder 97 intended for cooperation with the frustoconical recess 36 formed in the grip 30 of the pin carrier clamp. At the centre of the shoulder 97 a threaded rod 98 is fixed by any known means. The threaded rod 98 is intended to pass through the clamp 4' fastening the pins 5' in a transverse plane relative to the spacer bar, and for this purpose comes into engagement with a nut 99.

As already mentioned, the external fixation bar 1 has a polygonal section. In the embodiment described here the bar shown in FIG. 3 has two parallel faces 101 and 102 disposed between the pair of jaws 6, each of these faces being followed by a face 103 and 104 inclined at 20° in such a manner as to follow the shape of the corresponding inclined side 54 of the bridge and of the corresponding inclined side 64 of each jaw.

In the variant shown in FIG. 4 it will be observed that the clip according to the invention can also be fixed on a cylindrical bar. For this purpose an intermediate part 110 is added between the jaws, the outer walls of which part correspond to the parallel faces 101 and 102 and also to the inclined faces 103 and 104 already described. The connection member 110 has two openings 111 and 112 of generally rectangular shape and of dimensions permitting the passage of the disc 84 fixed to the end of the tube 83. A slot 113 is provided over the entire length of the connection member 110, in such a manner as to give the latter a certain elasticity. In addition, on each side of the pair of jaws the connection member 110 is provided with an outwardly facing collar, not shown in the drawing, which is intended to hold it in the clip.

Referring to FIGS. 6 to 8 presenting another embodiment, an external fixation bar 100, having a circular section, a clamp having an upper grip 120 and a lower grip 130, a jaw 160 for positioning the clip along the bar, a securing device 170 enabling the clip to be fastened on the bar 100, and also an arrangement 180 for clamping the pins 5 can be seen again. The curved deflection member is shown under the general reference 140; it has an arrangement 190 for the angular fixation with respect to the jaw 160.

To go into detail, the upper and lower clamp grips 120 and 130 have a generally rectangular shape and are provided with a central passage 121, 131 for the clamping arrangement 180. The mutually facing surfaces of the grips are provided with parallel grooves 122, 132 intended for the passage of the pins 5 inserted into the bones.

The upper face of the upper clamp grip 120 is provided with a recess 123 for a screw head of the clamping arrangement 180 while its lower face presents two symmetric recesses 124, to prevent the rotation of the grips 120 and 130 in relation to one another, as detailed later on.

The upper face of the lower clamp grip 130 is provided with two recesses 135 for receiving two nibs 136 protruding into the recesses 124 of the upper grip and further receiving two springs 125 intended to spread the grips 120 and 130 one from another, in order to facilitate the introduction of the pins 5. The lower face of the lower grip 130 has a cylindrical hollow 137 in order to authorize the swivelling of the clamp (and consequently of the pins) with respect to the deflection member 140.

This deflection member 140 presents a cap, the cover 141 of which has a curvature corresponding to the cylindrical hollow 137 in the lower grip. The cover 141 further presents an oblong opening 142 authorizing the free passage of the clamping arrangement 180. The wall 143 of the cap has a cylindrical shape and possesses a slot 144 extending at one of the ends of the opening 142 and defining two protruding wings 145 and 146.

In the sectional view of FIG. 8, it will be noted that the jaw 160 is not shown in order to authorize the representation of the deflection member 140. Its wing 145 has a threaded opening 147 and its wing 146 has a passage 148 opening into an external recess 149 intended to receive the fixation arrangement 190 which is transversally disposed with respect to the oblong opening 142 and to the slot 144.

In this embodiment the jaw 160 is in one piece having a generally cylindrical shape; it has a transverse passage 161 for the fixation rod 100, which extends to a slot 162 defining two wings 163 and 164 and authorizing the jaw 160 to be clamped on the bar 100 by means of the clamping arrangement 170 for positioning the jaw along the fixation rod. As visible in FIG. 7, the jaw 160 has an upper circular shoulder 165 intended to cooperate with the wall 143 in order to clamp the deflection member 140 by means of the fixation arrangement 190. The superior face of the shoulder 165 presents an upper recess 166 for the clamping arrangement 180. The shoulder 165 externally presents a groove 167 intended to receive the fixation arrangement 190 which bounds the deflection member 140 with the jaw 160, and realized on a part of the circumference for reasons given later on.

The clamping arrangement 170, visible in section in FIG. 7, is disposed perpendicular to the slot 162 and is intended to bring closer the wings 163 and 164. It consists in a screw 171 having a head 172 embedded in a recess 168 of the wing 164 and a threaded portion passing through the wing 164 and engaging an internal thread in the wing 163.

The clamping arrangement 180 of FIGS. 6 and 7 consists in a screw 181, the head 182 of which is intended to rest on the recess 123 of the upper grip 120. The threaded portion of the screw 181 freely passes through the passages 121 and 131 in the upper and lower grips, through the oblong opening 142 and engages in a stud 183, the superior face of which moulds the curvature of the deflection member cover 141.

The fixation arrangement 190, visible in section in FIG. 8, consists in a screw 191, the head 192 of which is intended to rest on the recess 149 of the wing 146. The threaded portion of the screw 191 freely passes through the passage 148 and engages in the threaded opening 147 in the wing 145.

It is to be noted that the screw heads 172, 182 and 192 present the same hexagonal opening, to be clamped with the same tool. In addition some of these screw heads could present flutes on their periphery, in order to authorize a manual pre-clamping.

For the well-being of the patient, the various components of the clip according to the invention (such as the clip carrier clamp, the deflection member, the jaw, and the angle drive means) have no sharp edges and are made of aluminum or other light alloy in order to limit the weight of the apparatus.

Before being used in the course of the operation, the clip according to the invention is assembled in the manner illustrated in the drawing, with or without an angle drive means depending on requirements.

In the course of the actual operation the surgeon inserts sets of pins into each bone fragment, applying known techniques. In the embodiment shown in FIGS. 2 to 5 each set of pins 5 is held in a plane by means of the clamp 4 and is positioned relative to the bar 1 by taking advantage of the continuous orientation facilitied of the clamp in the direction of the arrow B, through the relative positioning of the frustoconical recess 36 of the clamp grip 30 and of the corresponding frustoconical shoulder 41 of the curved deflection member 40. The nut 81 is then locked on the external screwthread 43 of the hollow shaft 42.

The locking of the angular pivoting of the clamp in the direction of the arrow A can be achieved in two ways.

Firstly, in cases where the clip according to the invention is intended to be fixed on the fixation bar 1, it will be sufficient to clamp the positioning device 7 on the bar to effect simultaneously the fastening of the clip and angular locking in the direction of the arrow A. By acting on one of the screw heads 71, the pair of jaws 6 is in fact clamped in accordance with the arrows E in FIG. 1. The sliding of the inclined side 64 of each jaw on the inclined face 103 of the bar displaces the top part of the jaw in the direction of the arrow F (FIG. 3). Consequently the curved shoulder 61 of the jaw comes to bear against the corresponding curved shoulder 49 of the deflection member 40, which is thus locked.

In the second case, where the clip is intended to be slidable along the spacer bar, the jaws 6 will thus not be clamped against the latter. In order to lock the pivoting of the deflection member 40 in the direction of the arrow A, the screw 88 is operated to bring its head 89 to bear against the internal shoulder 44 of the hollow shaft 42 and to enable the central tube 83 to be moved upwards. As already stated, the tube 83 is fastened to a disc 84 bearing against the central portion 52 of the bridge and thus enabling said bridge 50 to be clamped in relation to the curved deflection member 40, which is thus locked in position.

The ring 87 of the O-ring type disposed around the central tube 83 serves to retain the latter insided the hollow shaft 42 when the screw 88 has not been placed in position.

It has already been mentioned above that the head 79 of the screw 78 of the positioning device 7, when locked in the central shaft 77, comes to bear against the internal shoulder 75 of the hollow shaft 70, in the arrangement shown in FIG. 4, thus leaving a gap i between the end of the hollow shaft 70 and the inside face of the head 71 of the central shaft 77.

The purpose of this configuration is to avoid overtightening of the jaws on the bar. When in face the surgeon wished to tighten one of the screw heads 71 of the hollow shaft 70 or of the central shaft 77, he will only be able to bring about a displacement eliminating the gap i. As soon as the end of the hollow shaft 70 comes to bear against the head of the central shaft 77, the entire positioning device 7 will turn freely in the openings 66 of the jaws because of the provision of the O-rings 74. When it is desired to loosen the positioning device 7, it is sufficient to act on one of the screw heads 71; the O-ring 74 of the other assembly remains locked because the resistant torque of the O-ring is greater than the unscrewing torque. A release limiter is thus provided, with the aid of which the clip jaws remain in a position such that the clip will slide along the bar. The possible displacement of the gap i corresponds to about two turns.

In the embodiment shown in FIGS. 6 to 8, the setting is effected in an analogous way as previously described. The pins 5 are maintained in a plane by means of the clamp grips 120 and 130. It is to be noted that the springs 125 tend to press the cylindrical hollow 137 on the cover 141, thus braking the movement of the clamp on the deflection member.

With such an assembly, the physician can separately adjust the swivelling of the clamp with respect to the deflection member, according to the arrow A, and the rotation of the clamp and of the deflection member with respect to the jaw 160, according to the arrow B. In order to facilitate the practician's work, it was attempted to dispose the heads 172 and 192 of screws 171 and 191 on the same side of the clip. Therefore along a part (comprised between about 90 to 180°) of the circumference of the shoulder 165, one realizes the groove 167 intended to receive the fixation arrangement 190. Consequently one limits between 0° and about 90 to 180° the rotation of the clamp according to the arrow B with respect to the deflection member.

It will be further noted that the clip can be moved along the bar 100 according to the arrow D and be turned with respect to the bar according to the arrow G, as long as the securing device 170 is not locked.

Moreover the securing arrangements 170, 180 and 190 could be replaced by devices with a screwing and unscrewing limiter, as described with respect to the variant of FIG. 4. In the embodiment shown in FIGS. 6 to 8, one could further use an angle drive means, inserted between the jaw 160 and the deflection member 140.

I claim:

1. A device for fastening and angularly positioning a set of bone pins with respect to a fixation bar, said device comprising:
   (a) a clamp for gripping said bone pins,
   (b) a deflection member, and
   (c) a jaw for positioning said clamp in a selected position along said fixation bar,
   wherein said deflection member is located between said clamp and said jaw,
   wherein said deflection member has a first face comprising a first rotation means and a second face opposite to said first face comprising a first curved guide means,
   wherein a first element selected from the group consisting of said clamp and said jaw has located thereon a complementary rotation means which cooperates with said first rotation means so as to ensure rotation of said clamp with respect to said jaw,
   wherein a second element different from said first element and selected from the group consisting of said clamp and said jaw has located thereon a complementary curved guide means which cooperates with said first curved guide means so as to ensure swivelling of said clamp with respect to said jaw,
   wherein said clamp comprises an upper clamp grip and a lower clamp grip which have central passages for a clamping arrangement, and
   wherein a third element selected from the group consisting of said upper clamp grip and said lower clamp grip is provided with projections intended to penetrate into corresponding recesses in a fourth element different from said third element and selected from the group consisting of said upper clamp grip and said lower clamp grip, so as to prevent rotation of said upper clamp grip with respect to said lower clamp grip.

2. A device according to claim 1, wherein said clamping arrangement comprises a hollow shaft fastened to said deflection member for cooperation with a further clamping means.

3. A device for fastening and angularly positioning a set of bone pins with respect to a fixation bar, said device comprising:
   (a) a clamp for gripping said bone pins,
   (b) a deflection member, and
   (c) a jaw for positioning said clamp in a selected position along said fixation bar,
   wherein said deflection member is located between said clamp and said jaw,
   wherein said deflection member has a first face comprising a first rotation means and a second face opposite to said first face comprising a first curved guide means,
   wherein a first element selected from the group consisting of said clamp and said jaw has located thereon a complementary rotation means which cooperates with said first rotation means so as to ensure rotation of said clamp with respect to said jaw,
   wherein a second element different from said first element and selected from the group consisting of said clamp and said jaw has located thereon a complementary curved guide means which cooperates with said first curved guide means so as to ensure swivelling of said clamp with respect to said jaw,
   wherein said clamp comprises an upper clamp grip and a lower clamp grip which have central passages for a clamping arrangement,
   wherein said deflection member is provided with a first frustoconical shoulder adapted for at least indirect cooperation with a corresponding first frustoconical recess in said first element (selected from the group consisting of said clamp and said jaw), wherein said first frustoconical shoulder and said first frustoconical recess have a central passage for a clamp shaft, and wherein said deflection member is provided with a curved guide means situated in planes parallel to said bar and adapted for at least indirect cooperation with said jaw for effecting positioning along said bar.

4. A device according to claim 3, wherein said jaw for effecting positioning along said bar is a clamshell-type jaw having two symmetrical parts separated by a bridge having a central opening, each of said two symmetrical parts having a shape adapted to cooperate with a complementary shape, respectively, of said jaw.

5. A device according to claim 4, wherein said guide means comprises at least one curved skid adapted to slide along a hollow having a curvature corresponding to the curvature of said skid and formed within said bridge.

6. A device according to claim 4, wherein said bridge and said two symmetrical parts of said jaw together form a shape corresponding to the shape of the cross-section of said fixation bar.

7. A device according to claim 4, wherein said bridge and said two symmetrical parts of said jaw together form a shape corresponding to the shape of the cross-section of an intermediate part having a central passage adapted to receive a fixation bar.

8. A device according to claim 4, wherein said clamping arrangement comprises a central tube connecting said bridge and a screw (88).

9. A device according to claim 3, and including also an angle drive means which is located between said jaw and said clamp and which is suitable for changing the angular orientation of said clamp with respect to said bar,
   wherein said angle drive means has a further frustoconical opening and a further frustoconical shoulder situated in separate planes and adapted for cooperation respectively with said first frustoconical shoulder and said first frustoconical recess.

10. A device for fastening and angularly positioning a set of bone pins with respect to a fixation bar, said device comprising:
   (a) a clamp for gripping said bone pins,
   (b) a deflection member, and
   (c) a jaw for positioning said clamp in a selected position along said fixation bar,
   wherein said deflection member is located between said clamp and said jaw, wherein said deflection member has a first face comprising a first rotation means and a second face opposite to said first face comprising a first curved guide means, wherein a first element selected from the group consisting of said clamp and said jaw has located thereon a complementary rotation means which cooperates with said first rotation means so as to ensure rotation of said clamp with respect to said jaw, wherein a second element different from said first element and selected from the group consisting of said clamp and said jaw has located thereon a complementary curved guide means which cooperates with said first curved guide means so as to ensure swivelling of said clamp with respect to said jaw, wherein said clamp comprises an upper clamp grip and a lower clamp grip which have central passages for a clamping arrangement, and wherein said deflection member comprises a cylindrical wall for cooperation with a corresponding shoulder in said jaw and wherein said deflection member presents a curved cover for cooperation with a hollow having a corresponding curvature in said lower clamp grip, said hollow having an oblong-shaped opening.

11. A device according to claim 10, wherein said wall presents a slot extending from one end of said oblong-shaped opening, so as to form two wings adapted to receive a fixation arrangement for clamping said deflection member onto said jaw.

12. A device according to claim 11, wherein said corresponding shoulder in said jaw presents an external groove adapted to receive said fixation arrangement so as to limit rotation of said deflection member with respect to said jaw.

13. A device according to claim 10, wherein said jaw for positioning along said fixation bar has (a) a transverse passage located therein with a shape corresponding to the shape of said fixation bar, and (b) a slot which extends from said transverse passage so as to form two wings adapted to receive a clamping arrangement.

14. A device according to claim 13, and including also at least one screwing and unscrewing limiter which acts in cooperation with a fixation arrangement.

15. A device according to claim 14, wherein said fixation arrangement comprises a hollow shaft adapted to receive a central shaft having a screw thread.

16. A device according to claim 15, wherein said screwing and unscrewing limiter comprises a connection between said hollow shaft and said central shaft and an O-ring.

17. A device according to claim 16, wherein said connection between said hollow shaft and said central shaft is a screw having dimensions such that a gap is formed between one end of said hollow shaft and the inner face of the head of said central shaft.

* * * * *